(12) United States Patent
He et al.

(10) Patent No.: US 6,307,912 B1
(45) Date of Patent: Oct. 23, 2001

(54) METHODS AND APPARATUS FOR OPTIMIZING CT IMAGE QUALITY WITH OPTIMIZED DATA ACQUISITION

(75) Inventors: Hui David He, Waukesha; Thomas L. Toth, Brookfield, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/450,362

(22) Filed: Nov. 29, 1999

(51) Int. Cl.[7] .................................................. G01N 23/00
(52) U.S. Cl. .................................................. 378/19; 378/4
(58) Field of Search ............................................ 378/4, 19

(56) References Cited

U.S. PATENT DOCUMENTS

| | | |
|---|---|---|
| 5,379,333 | 1/1995 | Toth . |
| 5,400,378 | 3/1995 | Toth . |
| 5,416,815 | 5/1995 | Hsieh . |
| 5,828,719 | 10/1998 | He et al. . |
| 5,933,540 | 8/1999 | Lakshminarayanan et al. . |

Primary Examiner—Craig E. Church
(74) Attorney, Agent, or Firm—Armstrong Teasdale LLP; Christian G. Cabou

(57) ABSTRACT

A method is described for optimizing signal-to-noise performance of an imaging system, including the steps of scout-scanning an object to obtain scout scan data; determining a plurality of normalized x-ray input signal factors using the scout scan data; using the normalized x-ray input signal factors to determine at least one system input signal; selecting at least one gain for the object scan using the system input signal; and applying the selected gain corresponding to the system input signal in the object scan.

30 Claims, 2 Drawing Sheets

METHODS AND APPARATUS FOR OPTIMIZING CT IMAGE QUALITY WITH OPTIMIZED DATA ACQUISITION

BACKGROUND OF THE INVENTION

This invention relates generally to computed tomography (CT) imaging and, more particularly, to methods and apparatus for optimizing image quality in a CT system under low signal conditions.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

When scanning is performed under low signal conditions, electronics noise can cause low signal imaging artifacts. It is known to apply gain to scan signals to reduce low-signal artifacts. Too high a gain, however, can result in over-ranging, which also causes imaging artifacts. Other factors, for example, x-ray tube output current and output voltage and detector slice thickness, also are known to affect image quality and can make it difficult to select a gain appropriate for avoiding image artifacts. It would be desirable to provide a method for optimizing gain relative to input signal to avoid both low-signal artifacts and over-ranging artifacts.

BRIEF SUMMARY OF THE INVENTION

There is therefore provided, in one embodiment, a method for optimizing signal-to-noise performance of an imaging system, including the steps of scout-scanning an object to obtain scout scan data; determining a plurality of normalized x-ray input signal factors using the scout scan data; using the normalized x-ray input signal factors to determine at least one system input signal; selecting at least one gain for the object scan using the system input signal; and applying the selected gain corresponding to the system input signal in the object scan. The above-described method results in lower electronics noise while avoiding over-ranging. Thus both low-signal artifacts and over-ranging artifacts are prevented.

DETAILED DESCRIPTION OF THE INVENTION

Figure 1:
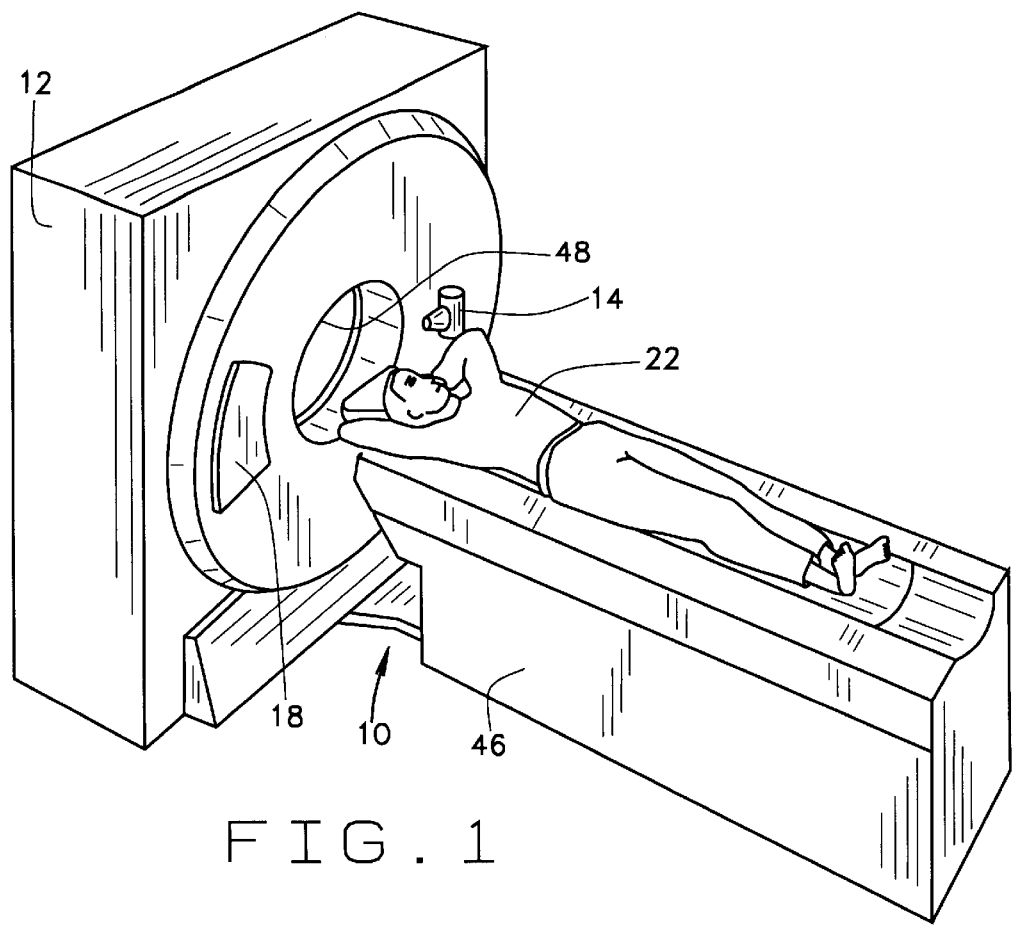
FIG. 1 is a pictorial view of a CT imaging system.
Figure 2:
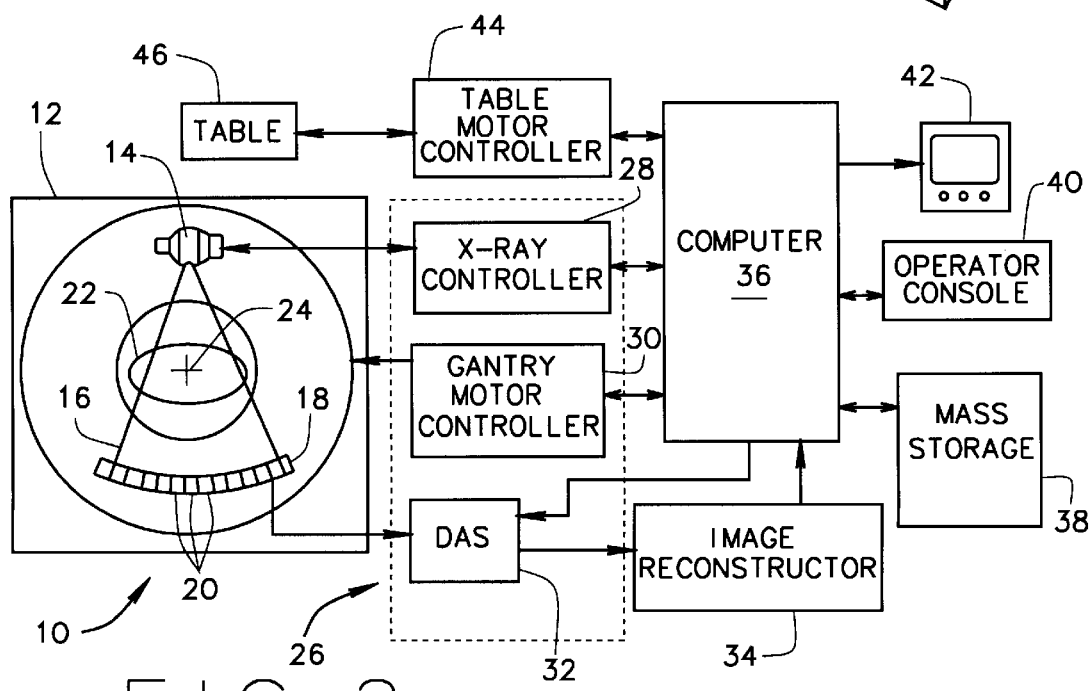
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14, for example an x-ray tube, that projects a beam of x-rays 16 toward a detector array 18 on the opposite side of gantry 12. Detector array 18 is formed by detector elements 20 that together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 that stores the image in a mass storage device 38.

Imaging system 10 includes system parameters that can be changed at imaging system 10 calibration. Computer 36 also receives commands and scanning parameters from an operator (not shown) via console 40 that has a keyboard. An associated cathode ray tube display 42 allows the operator to observe the reconstructed image and other data from computer 36. The operator-supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 12. Particularly, table 46 moves portions of patient 22 through gantry opening 48.

During a form of scanning known as scout scanning, gantry 12 is not rotated but remains stationary while table 46 moves through gantry opening 48. During a scout scan data is acquired for a view from a particular gantry angle relative to patient 22. Scout scanning is used, for example, to obtain a lateral view or an antero-posterior view of patient 22.

Figure 3:
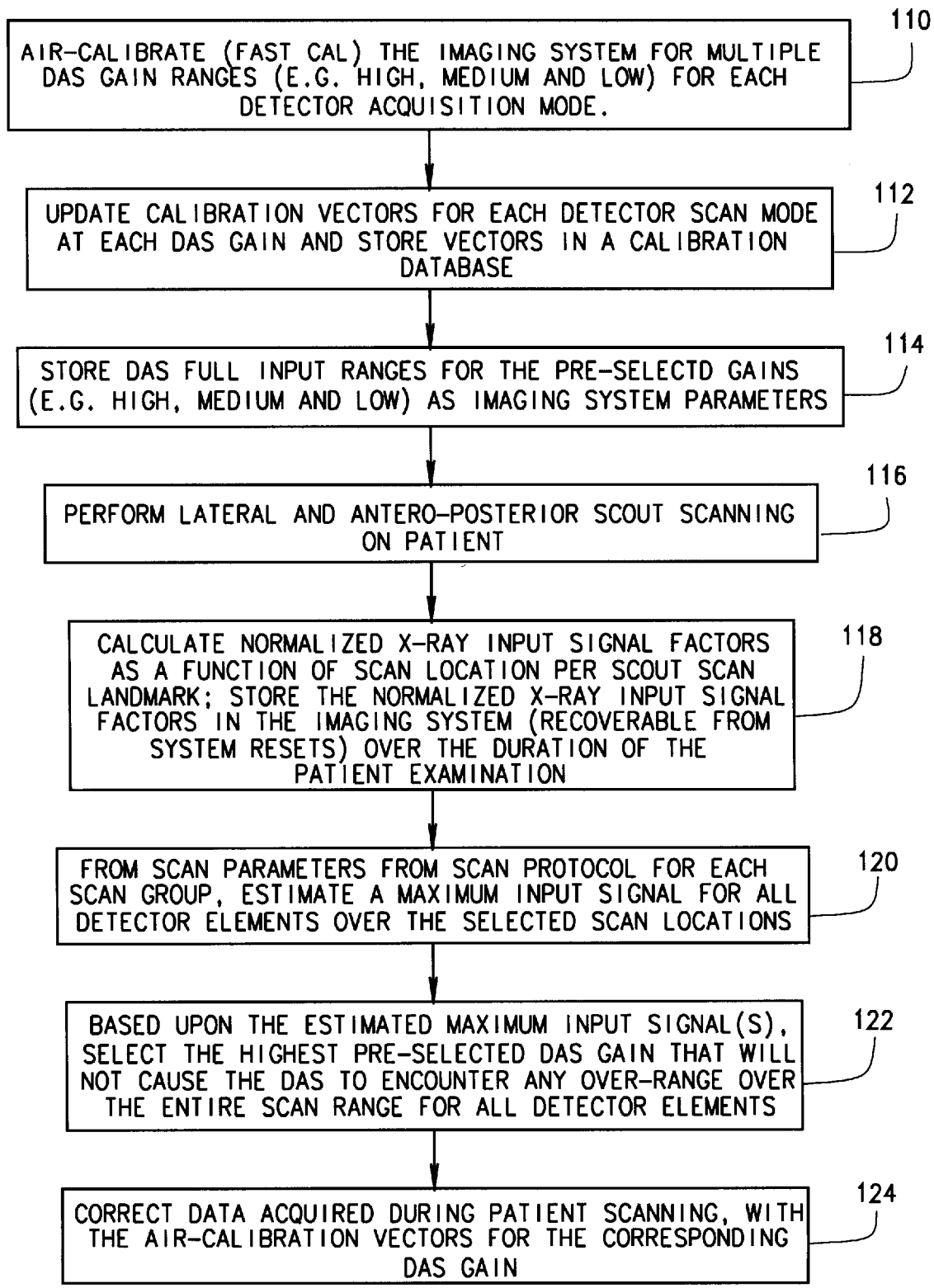
FIG. 3 is a flow diagram of an embodiment of a method for reducing imaging system electronic noise of the present invention.

Imaging system 10 includes a plurality of predetermined gains available for applying in data acquisition. Imaging system 10 is configured so that at least one gain corresponds to each detector array 18 slice thickness. A user can select modes for scanning, i.e. slice width and gain to be applied to scan data. In one embodiment and referring to FIG. 3, a method for optimizing data acquisition signal-to-noise performance of imaging system 10 includes air-calibrating 110 imaging system 10 to pre-select a set of gains from the predetermined gains associated with each detector array 18 slice thickness. The pre-selected gains can be designated, for example, as high, medium and low for each slice thickness.

Imaging system 10 parameters then are updated 112 with calibration vector data for each slice thickness corresponding to each pre-selected gain. For example, calibration vector data can be stored in a calibration database and can be used for scan data processing based on scan mode selections. Imaging system 10 parameters then are updated with DAS 32 full input signal ranges 114 for the pre-selected gains.

Lateral scout scanning is then performed 116 to obtain scout scan data pertaining to patient 22. Data quality is enhanced if antero-posterior scout scanning also is performed. Scout scan data is collected relative to a plurality of scout scan landmarks, e.g. patient 22 axial locations. Scout scan data then is used to determine at least one x-ray input signal factor that depends upon physical properties of patient 22 that affect x-rays detected by imaging system 10. Such properties include, for example, patient 22 dimensions, locations and positioning, x-ray attenuation densities and relative attenuation factors. Normalized x-ray input signal factors are determined 118 as functions of x-ray tube 14 voltage and current outputs, detector array 18 slice thickness, and DAS 32 gain. The normalized x-ray input signal factors are stored in imaging system 10 as a function of patient 22 axial location.

When an axial or helical scan is prescribed from console 40, the scanning parameters entered by the operator are used to estimate a maximum input signal 120 for all detector elements over patient 22 locations selected for scanning. The maximum input signal is determined by multiplying the normalized x-ray input signal factors for the selected patient 22 locations by requested x-ray tube 14 voltage and current output and detector array 18 slice thickness. A pre-selected DAS 32 gain then is determined 122 as the highest pre-selected gain that does not result in over-ranging when applied to the maximum input signal. Data acquired during scanning of patient 22 then is corrected 124 using the system parameters updated at calibration and corresponding to DAS 32 gain used for scanning.

The above-described method improves image quality under low signal conditions by selection of data acquisition amplification gains and full input signal ranges based on, for example, such parameters as scanned object location, geometric dimension, and relative attenuation factor. Image quality also can be improved by selecting input signal ranges and gains based on such scanning techniques as selection of x-ray voltage and current outputs, slice thickness, detector/DAS sampling frequency, and gantry rotation speed.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems, including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan; however, the invention may be used with a helical scan although more than 360 degrees of data are required. While the invention has been described in terms of various specific embodiments, those skilled in the art will recognize that the invention can be practiced with modification within the spirit and scope of the claims.

What is claimed is:

1. A method for reducing electronic noise during object scanning by a computed tomography imaging system, said method comprising the steps of:
    scout scanning the object to obtain scout scan data;
    determining at least one normalized x-ray input signal factor using the scout scan data;
    using the at least one normalized x-ray input signal factor to determine at least one system input signal;
    selecting at least one gain for the object scan using the at least one system input signal; and
    applying the at least one selected gain corresponding to the at least one system input signal in the object scan.

2. A method in accordance with claim 1 further comprising the steps of:
    calibrating the imaging system to update at least one system parameter before scout scanning; and
    correcting scan data collected in the object scan using the at least one updated system parameter.

3. A method in accordance with claim 2 wherein the imaging system is configured to detect x-rays in at least one slice of selectable thickness, each slice thickness corresponding to at least one gain of a plurality of gains, and calibrating the imaging system includes the steps of:
    air-calibrating the imaging system to specify for each slice thickness at least one pre-selected gain from the corresponding gains;
    updating the at least one system parameter using calibration vector data for each slice thickness corresponding to each pre-selected gain; and
    updating the at least one system parameter using input signal ranges corresponding to the pre-selected gains.

4. A method in accordance with claim 3 wherein the pre-selected gains are calibrated as high, medium and low relative to each slice thickness.

5. A method in accordance with claim 1 wherein the step of scout scanning an object to obtain scout scan data comprises performing a lateral scout scan to obtain scout scan data corresponding to a plurality of scout scan landmarks.

6. A method in accordance with claim 5 further comprising performing an antero-posterior scout scan.

7. A method in accordance with claim 1 wherein the imaging system is configured to produce at least one voltage output and at least one current output and to detect x-rays in at least one slice of selectable thickness, each slice thickness corresponding to at least one gain of a plurality of gains, and the step of determining at least one normalized x-ray input signal factor using the scout scan data comprises determining at least one x-ray input signal factor normalized over at least one of the voltage output, current output, slice thickness and gain as a function of object axial location.

8. A method in accordance with claim 7 wherein the at least one x-ray input signal factor is a function of at least one of the voltage output, current output, slice thickness and gain.

9. A method in accordance with claim 7 wherein the at least one x-ray input signal factor includes at least one of object dimensions, locations and positioning, x-ray attenuation densities and relative attenuation factors.

10. A method in accordance with claim 7 wherein object axial locations are determined from a plurality of scout scan landmarks.

11. A method in accordance with claim 1 wherein the imaging system includes at least one system parameter and the step of using the at least one normalized x-ray input signal factor to determine at least one system input signal comprises the step of estimating at least one maximum scan input signal using the at least one system parameter and the at least one normalized x-ray input signal factor.

12. A method in accordance with claim 11 wherein the step of selecting at least one gain for the object scan using the at least one system input signal comprises the step of selecting a gain for each maximum scan input signal.

13. A method in accordance with claim 12 wherein selecting a gain for each maximum scan input signal comprises selecting a highest pre-selected gain that does not result in over-ranging when applied.

14. A method in accordance with claim 11 wherein the at least one system parameter includes at least one of a voltage output requested for the object scan, a current output requested for the object scan, and a slice thickness requested for the object scan, and the step of estimating at least one maximum scan input signal using the at least one system parameter and the at least one normalized x-ray input signal factor comprises the step of multiplying at least one normalized x-ray input signal factor by at least one of the voltage output, current output, and slice thickness requested for the object scan.

15. A method in accordance with claim 11 wherein the step of estimating at least one maximum scan input signal using the at least one system parameter and the at least one normalized x-ray input signal factor comprises using at least one of data sampling frequency and gantry rotation speed.

16. An apparatus for reducing electronic noise during an object scan by a computed tomography imaging system, said apparatus configured to:
   scout scan the object to obtain scout scan data;
   determine at least one normalized x-ray input signal factor using the scout scan data;
   use the at least one normalized x-ray input signal factor to determine at least one system input signal;
   select at least one gain for the object scan using the at least one system input signal; and
   apply the at least one selected gain corresponding to the at least one system input signal in the object scan.

17. An apparatus in accordance with claim 16 further configured to:
   calibrate the imaging system to update at least one system parameter before scout scanning; and
   correct scan data collected in the object scan using the at least one updated system parameter.

18. An apparatus in accordance with claim 17 wherein the imaging system is configured to detect x-rays in at least one slice of selectable thickness, each slice thickness corresponding to at least one gain of a plurality of gains, and to calibrate the imaging system, said apparatus is configured to:
   air-calibrate the imaging system to specify for each slice thickness at least one pre-selected gain from the corresponding gains;
   update the at least one system parameter using calibration vector data for each slice thickness corresponding to each pre-selected gain; and
   update the at least one system parameter using input signal ranges corresponding to the pre-selected gains.

19. An apparatus in accordance with claim 18 configured to calibrate the pre-selected gains as high, medium and low relative to each slice thickness.

20. An apparatus in accordance with claim 16 wherein to scout scan an object to obtain scout scan data, said apparatus is configured to perform a lateral scout scan to obtain scout scan data corresponding to a plurality of scout scan landmarks.

21. An apparatus in accordance with claim 20 further configured to perform an antero-posterior scout scan.

22. An apparatus in accordance with claim 16 wherein the imaging system is configured to produce at least one voltage output and at least one current output and to detect x-rays in at least one slice of selectable thickness, each slice thickness corresponding to at least one gain of a plurality of gains, and to determine at least one normalized x-ray input signal factor using the scout scan data, said apparatus is configured to determine at least one x-ray input signal factor normalized over at least one of the voltage output, current output, slice thickness and gain as a function of object axial location.

23. An apparatus in accordance with claim 22 further configured to determine the at least one x-ray input signal factor as a function of at least one of voltage output, current output, slice thickness and gain.

24. An apparatus in accordance with claim 22 configured to determine as at least one x-ray input signal factor at least one of object dimensions, locations and positioning, x-ray attenuation densities and relative attenuation factors.

25. An apparatus in accordance with claim 22 configured to determine object axial locations from a plurality of scout scan landmarks.

26. An apparatus in accordance with claim 16 wherein the imaging system includes at least one system parameter and to use the at least one normalized x-ray input signal factor to determine at least one system input signal, said apparatus is configured to estimate at least one maximum scan input signal using the at least one system parameter and the at least one normalized x-ray input signal factor.

27. A method in accordance with claim 26 wherein to select at least one gain for the object scan using the at least one system input signal said apparatus is configured to select a gain for each maximum scan input signal.

28. A method in accordance with claim 27 wherein to select a gain for each maximum scan input signal, said apparatus is configured to select a highest pre-selected gain that does not result in over-ranging when applied.

29. An apparatus in accordance with claim 26 wherein the at least one system parameter includes at least one of a voltage output requested for the object scan, a current output requested for the object scan, and a slice thickness requested for the object scan, and to estimate at least one maximum scan input signal using the at least one system parameter and the at least one normalized x-ray input signal factor, said apparatus is configured to multiply at least one normalized x-ray input signal factor by at least one of the voltage output, current output, and slice thickness requested for the object scan.

30. An apparatus in accordance with claim 26 wherein said apparatus is configured to estimate at least one maximum scan input signal using at least one of data sampling frequency and gantry rotation speed.

* * * * *